United States Patent
Ashton

(10) Patent No.: US 6,379,650 B1
(45) Date of Patent: Apr. 30, 2002

(54) TECHNETIUM 99M-N$_2$S$_2$-CONGO RED COMPLEXES UTILIZING DIAMIDE DITHIOLATE LIGAND SYSTEMS FOR RADIOIMAGING

(76) Inventor: Wesley Scott Ashton, 8549 Blackfoot Ct., Lorton, VA (US) 22079

( * ) Notice: Subject to any disclaimer, the term of this patent is extended or adjusted under 35 U.S.C. 154(b) by 0 days.

(21) Appl. No.: 09/927,489

(22) Filed: Aug. 13, 2001

Related U.S. Application Data

(63) Continuation-in-part of application No. 09/810,450, filed on Mar. 19, 2001, now abandoned.

(51) Int. Cl.[7] .............................................. A61K 36/14
(52) U.S. Cl. ...................... 424/9.1; 424/1.11; 424/1.65; 534/14
(58) Field of Search ............................... 424/1.11, 1.65, 424/9.1, 9.3, 9.4, 9.5, 9.6, 9.7, 9.8; 534/7, 10–16; 562/30, 67

(56) References Cited

U.S. PATENT DOCUMENTS

| | | | |
|---|---|---|---|
| 4,746,505 A | 5/1988 | Jones et al. | 424/1.1 |
| 5,039,511 A | 8/1991 | Quay et al. | 424/1.1 |
| 5,080,883 A | 1/1992 | Lyle et al. | 424/1.1 |
| 5,095,111 A | 3/1992 | Lever et al. | 540/544 |
| 6,168,776 B1 | 1/2001 | Klunk et al. | 424/1.11 |

OTHER PUBLICATIONS

Han, H., Cheon–Gyn, C., and Landsbury, P.T.: Technetium Complexes for the Quantification of Brain Amyloid, J.Am. Chem.Soc. 118:4506–7, 1996.

Fritzberg et al.: "Specific and Stable Labeling of Antibodies with Technecium—99m with a Diamide Dithiolate Chelating Agent." Proc. Natl. Acad.Sci. 85:4025–4029, 1988.

Lever et al.: Synthesis of a Novel BiFunctional Chelate Designed for Labeling Proteins with Technetium—99m. Tetra. Lett. 29:3219–3222, 1988.

Lever et al.: "Pulmonary Accumulation of Neutral Diamine Dithiol Complexes of Technetium—99m." J. Pharm. Sci. 83:802–809, 1994.

Baidoo et. al. BiFunctional Chelator for Facile Preparation of Neutral Technetium Complexes. Bioconjugate Chem. 5:114–118, 1994.

Primary Examiner—Dameron L. Jones
(74) Attorney, Agent, or Firm—Wesley Scott Ashton

(57) ABSTRACT

The present invention discloses a group of technetium 99m-N$_2$S$_2$-congo red complexes that utilize diamide dithiolate ligand systems to synthesize compounds for radioimaging. The complexes have the general formula:

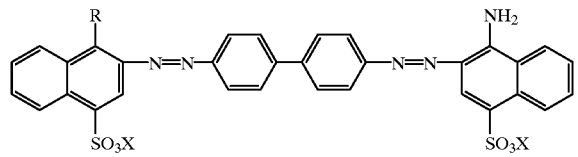

wherein R represents a diamide dithiolate ligand system and X represents a cation. Specifically, disclosed are two moieties, wherein the first moiety utilizes a $^{99m}$Tc-4,5-bis(thioacetamido)pentanoyl(N$_2$S$_2$) ligand system conjugated to the congo red molecule. In a preferred embodiment, the second moiety utilizes a 4-[2,5,5-Trimethyl-4-aza-2-mercaptohexyl]-6,6-dimethyl-2-thiomorpholinone ligand system conjugated to the congo red molecule. Both moeities can be used for radioimaging amyloid in animals and man by either intravenous or intrathecal administration.

17 Claims, 3 Drawing Sheets

TECHNETIUM 99M-N₂S₂-CONGO RED COMPLEXES UTILIZING DIAMIDE DITHIOLATE LIGAND SYSTEMS FOR RADIOIMAGING

This application is a continuation-in-part of application Ser. No. 09/810,450, filed Mar. 19, 2001, now abandoned.

BACKGROUND OF THE INVENTION

1. The background of the invention pertains to the field of medical radioimaging; specifically, the radioimaging of amyloid proteins in biological organisms such as human patients using a Technecium isotope ($^{99m}$Tc) for radiolabeling congo red. The present invention discloses multiple $^{99m}$Tc-labeled congo red complexes and their precursors utilizing various diamide dithiolate ligand systems and disclosing convenient methods for making these products, thereby providing a cost effective and practical means for enhancing the radioimaging of amyloid by standard nuclear medicine techniques.

2. Description of the Prior Art

Amyloidosis is a term applied to a group of disorders (e.g. chronic inflammatory diseases, infections, and neoplasms) associated with the deposition of insoluble fibrillar proteins within various organs of the body, which results in significant morbidity and mortality. There are other diseases such as Alzheimer's disease that are associated with nonsystemic, organ specific amyloid deposits. Before radioimaging, the only practical means for diagnosing amyloid in the tissues was by tissue biopsy.

In 1922, it was demonstrated that intravenous congo red cleared faster from the blood of patients having significant systemic amyloidosis. In the 1960's, radiolabeled congo red was used to photometrically determine plasma clearance and in 1962, scientists demonstrated localization of amyloid deposits in the livers and spleens of patients with systemic amyloidosis using nuclear medicine radioimaging techniques and I$^{131}$-radiolabeled congo red. However, I$^{131}$ is a radioisotope having a significantly long half-life. Recently, Han et al. disclosed a $^{99m}$Tc-radiolabeled congo red complex utilizing a bipyridyl analogue (*J. Am. Chem. Soc.*, 118:4506–4507, 1996). Technicium-99m radioisotope has the advantage of a short half-life; however, the bipyridyl analogue of congo red disclosed by Han et al. is apparantly difficult to produce. The present application discloses several $^{99m}$Tc-radiolabeled congo red complexes and their precursors that utilize one of multiple diamide dithiolate (N₂S₂) ligand systems conjugated to the Congo red molecule. These $^{99m}$Tc-radiolabeled congo red complexes and their precursors utilize diamide dithiolate (N₂S₂) ligand systems that rely upon well defined chemistries and are practical to produce for onsite use. Some of the precursors are suitable for storage as stable salts, and can be complexed with $^{99m}$Tc when needed.

SUMMARY OF THE INVENTION

It is a primary object of the invention to overcome the shortcomings of the prior art radiolabeled congo red complexes by providing a $^{99m}$Tc-radiolabeled congo red complex that utilizes a diamide dithiolate (N₂S₂) ligand system.

It is a primary object of the invention to provide a $^{99m}$Tc-radiolabeled congo red complex utilizing a diamide dithiolate (N₂S₂) ligand system that is practical to produce.

It is a primary object of the invention to provide a $^{99m}$Tc-radiolabeled congo red complex utilizing a diamide dithiolate (N₂S₂) ligand system that is practical to use as a radioimaging agent in warm blooded animals and human patients.

It is a primary object of the invention to provide a $^{99m}$Tc-radiolabeled Congo red complex utilizing a diamide dithiolate (N₂S?) ligand system that is suitable for intravenous or intrathecal administration to a warm blooded animal or human patient.

It is a primary object of the invention to provide a congo red complex precursor utilizing a diamide dithiolate (N₂S₂) ligand system that forms a stable salt for long term storage and that can be subsequently complexed with $^{99m}$Tc to form a $^{99m}$Tc-radiolabeled Congo red complex utilizing a diamide dithiolate (N₂S₂) ligand system.

DESCRIPTION OF THE DRAWINGS OF THE INVENTION

Figure 3:
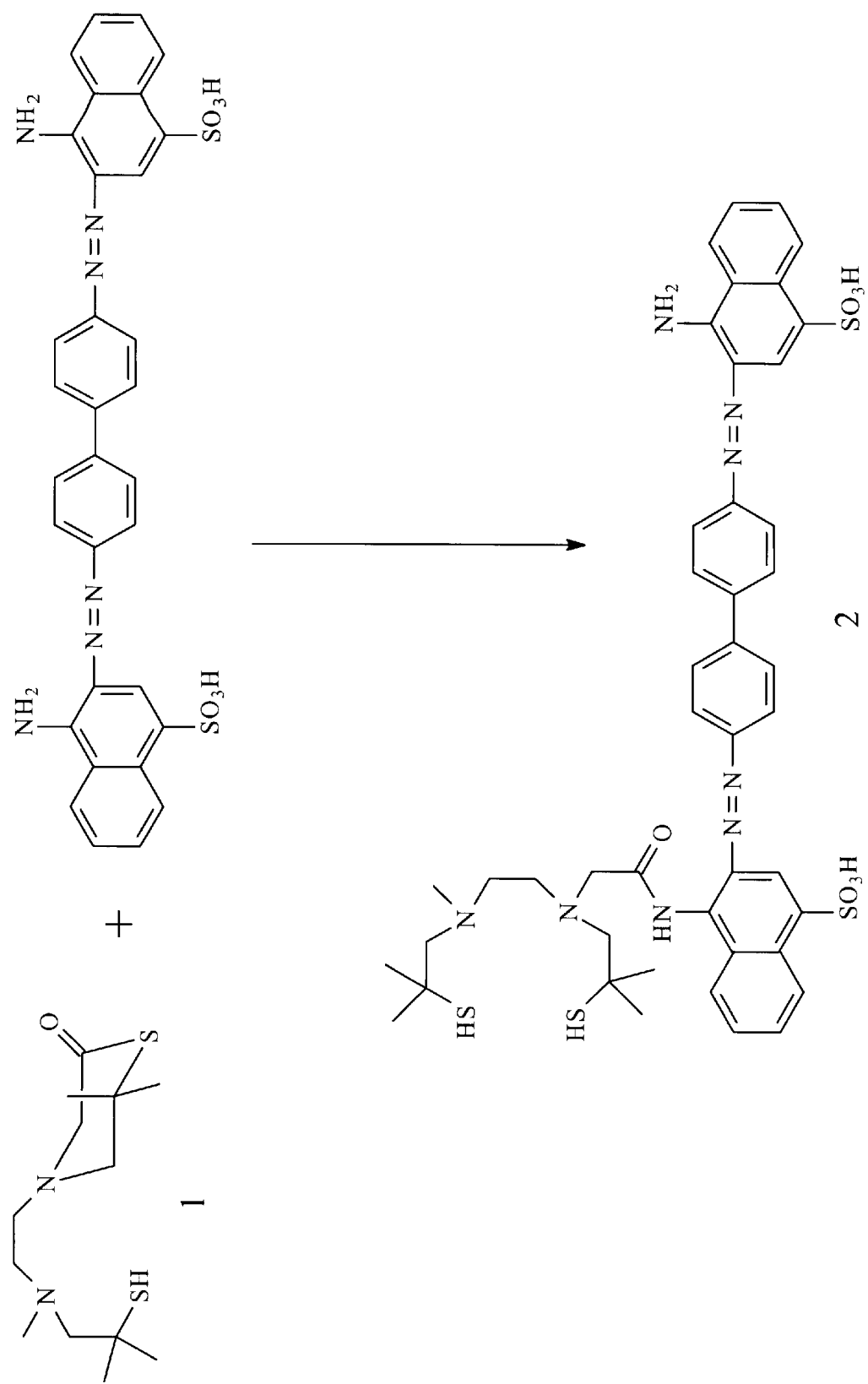

FIG. 3 illustrates the first step in the synthesis of compound 3, a $^{99m}$Tc-BCA-congo red complex, wherein compound 1, a diamide dithiolate ligand system known as BCA, and Congo red react together to form an intermediate compound, compound 2.

Figure 4:
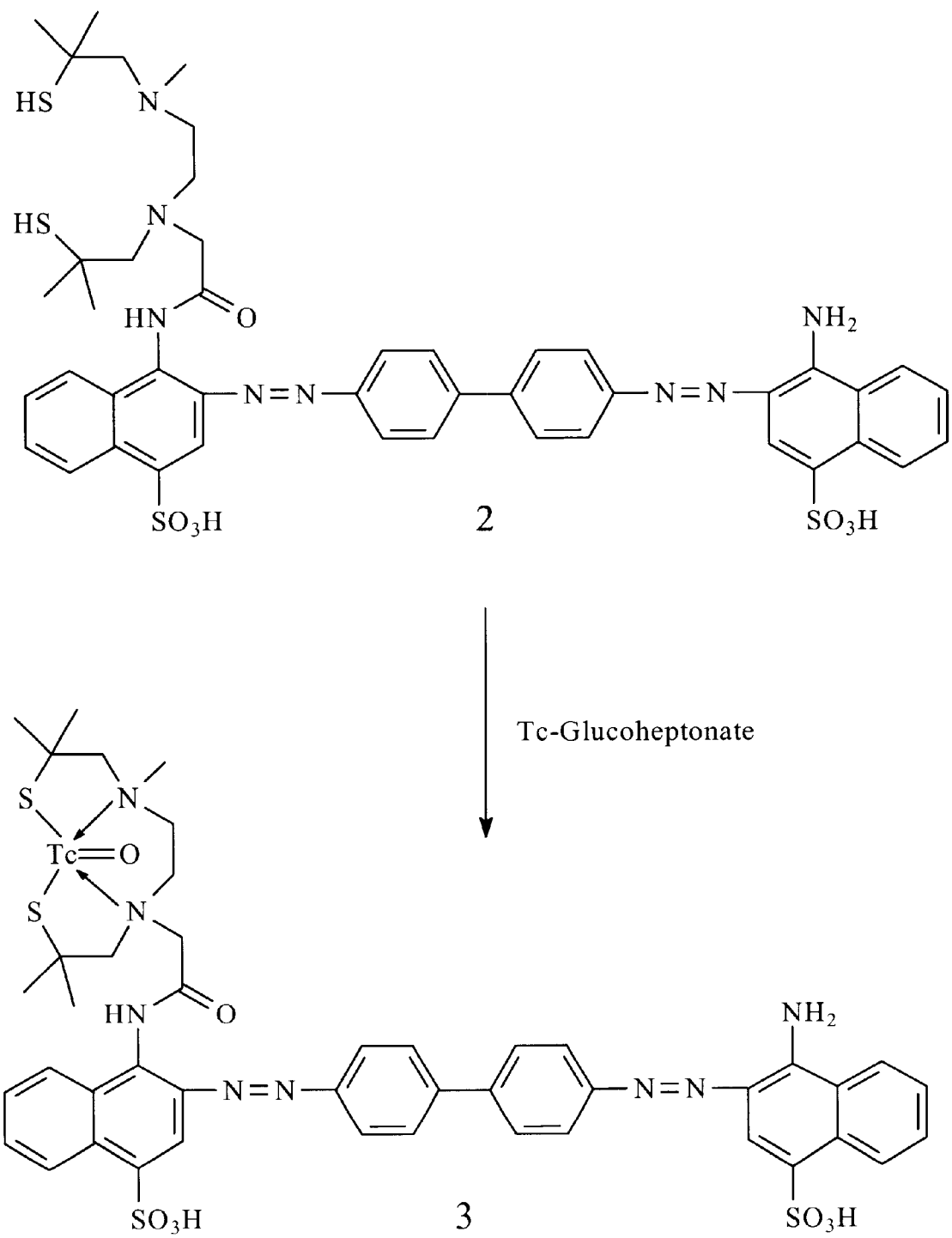

FIG. 4 illustrates the second step in the systhesis of compound 3, wherein compound 2 is complexed with radioactive technechium ($^{99m}$Tc).

DESCRIPTION OF THE PREFERRED INVENTION AND EMBODIMENTS

Figure 1:
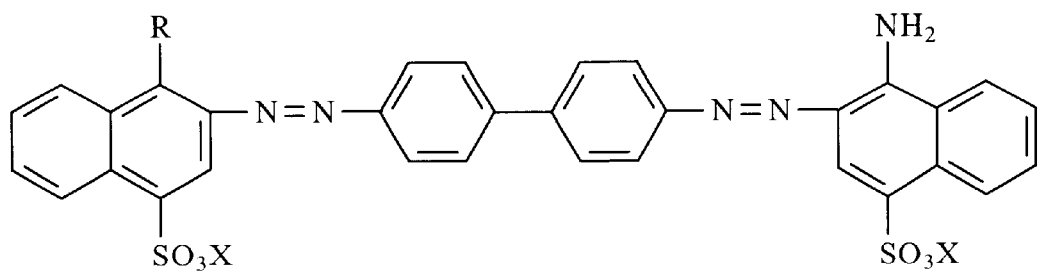
FIG. 1 illustrates the invention, a radioimaging agent compound consisting of a congo red molecule conjugated to a diamide dithiolate ligand system where R represents the diamide dithiolate ligand system conjugated to an amino group that is bonded to the benzene ring of the congo red molecule and X represents a cation such as sodium, potassium or hydrogen.

Refering now to the drawings, FIG. 1 illustrates the invention, being a $^{99m}$Tc-radiolabeled congo red complexed compound utilizing a diamide dithiolate (N₂S₂) ligand system, wherein the R group shown is a diamide dithiolate ligand system and the amino group of the congo red molecule to which the ligand covalently binds.

Figure 2:
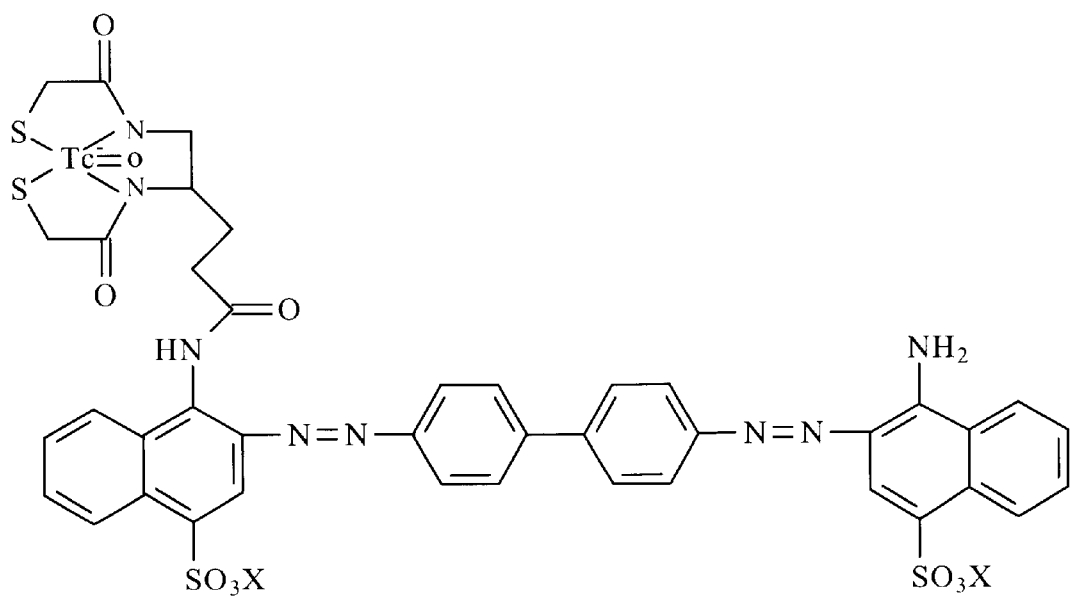
FIG. 2 illustrates the compound of FIG. 1 wherein the R group is $^{99m}$Tc-4,5-bis(thioacetamido)pentanoyl conjugated to the amino group of the congo red molecule and X is a cation such as sodium, potassium, or hydrogen.

FIG. 2 illustrates one embodiment of the invention wherein the bifunctional chelating R group of FIG. 1 is a $^{99m}$Tc-4,5-bis(thioacetamido)pentanoyl(N₂S₂) ligand system conjugated to the congo red molecule via an amino group of the congo red molecule. This first embodiment is produced by utilizing a well defined chemistry described by Fritzberg et al. (*Proc. Natl. Acad. Sci.* 85:4025–4029, 1988) and modified to the present application.

To a mixture of 25 µl of 4,5-bis(benzoylthioacetamido) pentanoic acid (1.0 mg/ml solution in 90% CH₃CN) and 100 µl of 1 M NaOH, add 100 mCi of sodium[$^{99m}$Tc] pertechnetate in 1.0 ml of saline (0.9% NaCl). Then 1.0 mg of sodium dithionite (0.10 ml of freshly prepared 10 mg/ml solution) is added, and the mixture is heated at 75° C. for 15 min. The pH is adjusted to about 6 with 0.10 ml of 1 M HCl and 0.30 ml of 0.2 M sodium phosphate buffer (pH 6.0). Then 10.0 mg of 2,3,5,6-tetrafluorophenol (0.10 ml of a 100 mg/ml solution in 90% CH₃CN) and 12.5 mg of 1-(3-dimethylaminopropyl)-3-ethylcarbodiimide (0.10 ml of a 125.0 mg/ml solution in 90% CH₃CN) is added and the solution subsequently heated at 75° C. for 30 min. The resulting tetrafluorophenyl active ester derivative of $^{99m}$Tc-4,5-bis(thioacetamido)pentanoate is subsequently purified by loading the reaction mixture on a conditioned C₁₈ cartridge, washing eight times with a 2.0 ml of 20% (vol/vol) ethyl alcohol/0.01 M sodium phosphate pH 7.0, and eluting with 100% $CH_3CN$. The solvent is subsequently evaporated under a stream of $N_2$. Then 0.5 ml of congo red at about 2.5 mg/ml and 0.50 ml of 0.2 M sodium phosphate (pH 9.0) are added for conjugation. After 15 min at room temperature, 25 mg of lysine (0.25 mg of a 250-mg/ml solution at pH 9.0) is added to quench unreacted ester.

The resulting $^{99m}$Tc-4,5-bis(thioacetamido)pentanoyl-congo red complex is purified by passage through a G-25 Sephadex column (Pharmacia) equilibrated with non-toxic phosphate-buffered physiologic saline to produce a diagnostic composition suitable for injection as a non-toxic salt. When used as a radioimaging agent, the purified $^{99m}$Tc-4,5-bis (thioacetamido)pentanoyl-congo red product would be closed intravenously for SPECT imaging in the range of approximately 2–10 µg/kg for humans and warm blooded animals. Nuclear medicine SPECT imaging is subsequently performed using standard imaging techniques. Images can be attained at predetermined time intervals such as hours 0, 1, 4, 8, 12 and 24. Other suitable nuclear medicine imaging techniques and other predetermined time intervals can be used as well.

Alternately, intrathecal administration using standard intrathecal injection techniques is performed using the purified $^{99m}$Tc-4,5-bis(thioacetamido)pentanoyl-congo red product dosed in a lower range of approximately 0.1–2 µg/kg for humans and warm blooded animals. Intrathecal administration bypasses the blood-brain barrier and is used for detecting amyloid deposits in the brain. The subsequent nuclear medicine imaging is performed using the same method as used when the $^{99m}$Tc-4,5-bis(thioacetamido)pentanoyl-congo red product was administered intravenously.

In an alternate and preferred embodiment of the invention, the diamide dithiolate ligand system moitey utilized is the bifunctional chelate moiety first described by Lever et al. (*Tetra Lett.* 29:3219–3222).

Lever et al.'s bifunctional chelate agent moiety, 4-[2,5,5-Trimethyl-4-aza-2-mercaptohexyl]-6,6-dimethyl-2-thiomorpholinone (hereafter refered to as "BCA"), shown as compound 1 in FIG. 3, is designed to couple to free amino groups of proteins and peptides under mild conditions to permit specific labeling with technetium-99m utilizing the two step synthesis scheme shown in FIGS. 3 and 4. The synthesis of BCA is described by Lever et al. in U.S. Pat. No. 5,095,111, which is incorporated herein by reference.

The first step in the synthesis of the desired $^{99m}$Tc-BCA-congo red complex (compound 3 in FIG. 4) is shown in FIG. 3 and begins with adding 0.5 ml of a solution of congo red at about 2.5 mg/ml in acetonitrile to previously prepared BCA (50 mg, 0.16 mmol) in a vial and stir at room temperature for 2 h. The mixture is chromatographed by short path silica chromatography using 2:3 hexane/ether as solvent. The resulting precursor compound, the congo red adduct of BCA (compound 2 in FIG. 3), may be synthesized and used freshly or sythesized and processed for long term storage as a stable salt. For example, the addition of an ethanolic solution of oxalic acid to an ethanolic solution of the free base congo red adduct of BCA will produce a stable, conveniently storable oxalate salt. It is noted that compound 2 may form other suitably storable stable salts.

To synthesize the $^{99m}$Tc-BCA-congo red complex from compound 2 (as shown in FIG. 4), a Glucoheptonate Kit (Glucoscan, Dupont, N. Billerica, Mass.) is reconstituted by the addition of [$^{99m}$Tc]NaTcO$_4$ (3 ml, 12.3 mCi) obtained from a [$^{99}$]Mo/[$^{99m}$]Tc generator (Cintichem/Union Carbide) or other suitable source and allowed to stand 15 min. The resulting [$^{99m}$Tc]Tc-glucoheptonate (0.5 ml, 2.0 mCi) is transfered to either 0.5 ml of the fresh ethanolic solution of the Congo red adduct of BCA, or to a solution of 1 mg of the oxalate salt of the congo red adduct of BCA dissolved in a suitable amount of ethanol (about 0.5 ml or more). The mixture is vortexed for 1 min and then allowed to stand at room temperature for 10 min.

The resulting $^{99m}$Tc-BCA-congo red complex is purified by HPLC and a the volatile solvent removed by evaporation under reduced pressure. Phoshpate-buffered physiologic saline is mixed with the residue to an reconstitute the purified $^{99m}$Tc-BCA-congo red complex to provide a suitable diagnostic composition for injection as a non-toxic salt. When used as a radioimaging agent, the purified $^{99m}$Tc-BCA-congo red complex would be dosed intravenously for SPECT imaging in the range of approximately 2–10 µg/kg for humans and warm blooded animals. Nuclear medicine SPECT imaging is subsequently performed using standard imaging techniques. Images can be attained at predetermined time intervals such as hours 0, 1, 4, 8, 12 and 24. Other suitable nuclear medicine imaging techniques and other predetermined time intervals can be used as well.

Alternately, intrathecal administration using standard intrathecal injection techniques is performed using the purified $^{99m}$Tc-BCA-congo red complex dosed in a lower range of approximately 0.1–2 µg/kg for humans and warm blooded animals. Intrathecal administration bypasses the blood-brain barrier and is used for detecting amyloid deposits in the brain. The subsequent nuclear medicine imaging is performed using the same method as used when the $^{99m}$Tc-BCA-congo red complex was administered intravenously.

Lastly, it is noted that the specific embodiments evinced herein in the specification and drawings are merely illustrations of the preferred embodiment and principal variation of the invention, being directed to $^{99m}$Tc-radiolabeled congo red complexes that utilize a diamide dithiolate ($N_2S_2$) ligand system. The $^{99m}$Tc-radiolabeled congo red complex compound is given parenterally to a human patient or to a warm blooded animal and then subsequent nuclear medicine radioimaging is performed using standard techniques to detect amyloid deposits as previously disclosed by the methods described above.

Preferably, intravenous administration of the compound is performed to detect systemic amyloid deposits, and intrathecal administration of the compound is performed to detect amyloid deposits in the brain; however, it is within the ability of one of ordinary skill in the art to use the intravenous administration of the $^{99m}$Tc-radiolabeled congo red complex compound to detect brain amyloid deposits.

Also, it is certainly within the ability of one of ordinary skill in the art to apply chemically similar diamide dithiolate ligand system moieties ($N_2S_2$) besides the 4,5-bis (thioacetamido)pentanoyl($N_2S_2$) ligand system and the BCA ligand system to form other $^{99m}$Tc-$N_2S_2$-congo red complex moieties. In this context, other diamide dithiolate ligand system moieties are defined as being chemically similar to the 4,5-bis(thioacetamido)pentanoyl($N_2S_2$) ligand system and/or the BCA ligand system if they form $^{99m}$Tc-N$_2$S$_2$-congo red complex moieties under the same or similar chemical conditions previously discussed above.

Therefore, the specification and drawings are not to be construed as limiting or restrictive, the full spirit and scope of the invention being further defined by the appended claims.

The invention claimed is:
1. A radioimaging agent compound of the formula

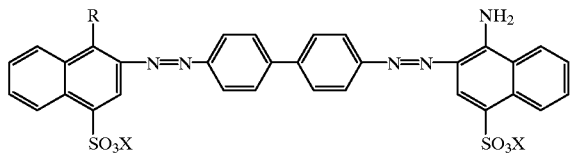

wherein
X represents a cation;
R is a group comprising a diamide dithiolate ligand system including Tc$^{99}$; and non-toxic salts thereof.

2. A radioimaging agent compound as recited in claim 1, wherein the cation X is selected from the group of hydrogen, potassium, and sodium.

3. A radioimaging agent compound as recited in claim 1, wherein the compound is of the formula

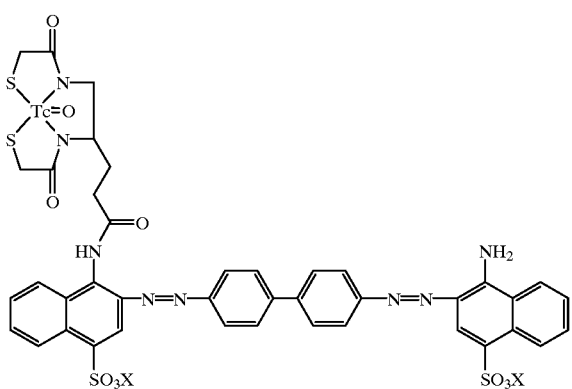

wherein X represents a cation.

4. A radioimaging agent compound as recited in claim 3, wherein the X cation is hydrogen.

5. A radioimaging agent compound as recited in claim 1, wherein the compound is of the formula

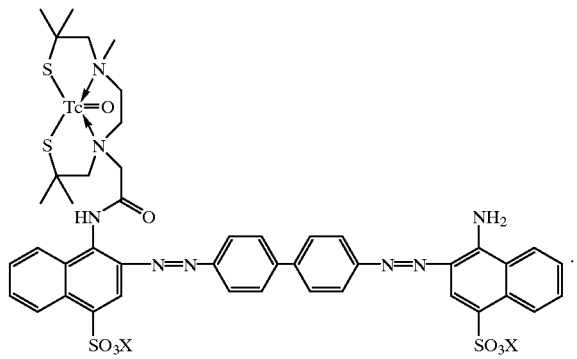

6. A stable salt suitable for long term storage, said stable salt comprising:

a congo red adduct of BCA capable of further processing to generate the radioimaging agent compound of claim 5.

7. A stable salt as recited in claim 6, wherein the stable salt is an oxalate salt.

8. A stable salt as recited in claim 6, wherein the Congo red adduct of BCA is of the formula

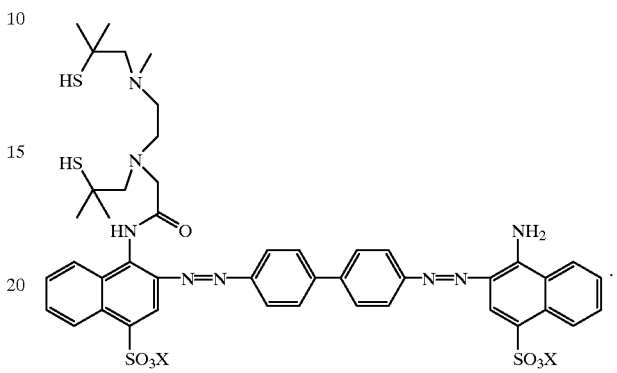

9. A stable salt as recited in claim 8, wherein the stable salt is an oxalate salt.

10. A diagnostic composition for administration to a warm-blooded animal or human patient, the composition comprising a congo red compound labeled with a Tc-99m diamine dithiolate (N$_2$S$_2$) bifunctional chelate, wherein the composition is suitable for injection into an animal or human patient to produce reliable visual imaging of amyloid.

11. A diagnostic composition as recited in claim 10, wherein the composition includes saline and is suitable for intravenous injection into an animal or human patient.

12. A diagnostic composition as recited in claim 10, wherein the composition includes buffered saline and is suitable for intrathecal injection into an animal or human patient.

13. A diagnostic composition as recited in claim 10, wherein said Tc-99m labeled congo red compound has the formula

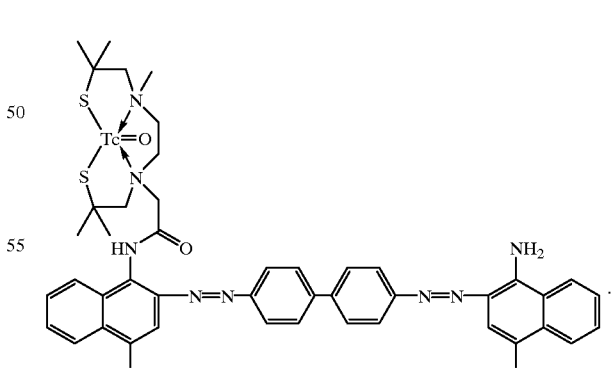

14. A diagnostic composition as recited in claim 10, wherein said Tc-99m labeled congo red compound has the formula

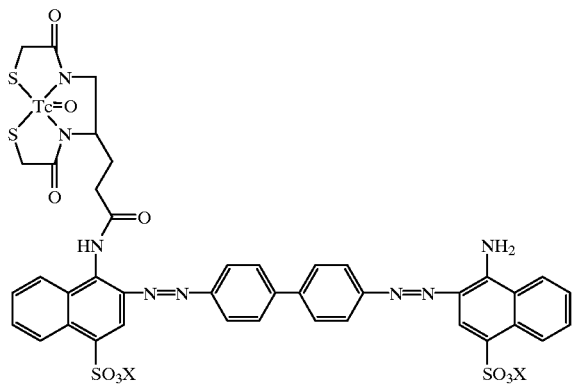

wherein X represents hydrogen.

15. A method for detecting amyloid deposits in an animal or human patient, the method comprising the steps of:

provinding a diagnostic composition suitable for injection into an animal or human patient, wherein the diagnostic composition includes a radiolabeled compound that comprises a diamine dithiolate ($N_2S_2$) bifunctional chelate conjugated to congo red and that emits detectable radiation and binds to amyloid deposits;

injecting the diagnostic composition parenterally into an animal or human patient; and scanning the animal or human patient for detectable radiation emitted by the radiolabeled compound with a scanner, wherein the scanning is performed at predetermined time intervals to reliably detect amyloid deposits by detecting radiation emitted by the radiolabeled compound.

16. A method for detecting amyloid deposits as recited in claim 15, wherein the injecting of the diagnostic composition is performed intravenously.

17. A method for detecting amyloid deposits as recited in claim 15, wherein the injecting of the diagnostic composition is performed intrathecally.

* * * * *